(12) United States Patent
Morales et al.

(10) Patent No.: US 8,133,227 B2
(45) Date of Patent: Mar. 13, 2012

(54) STERNUM CLOSURE DEVICE

(75) Inventors: Pedro Morales, Tuttlingen (DE); Dieter Weisshaupt, Immendingen (DE); Theodor Lutze, Balgheim (DE); Manfred Dworschak, Duerbheim (DE)

(73) Assignee: Aesculap AG, Tuttlingen (DE)

( * ) Notice: Subject to any disclaimer, the term of this patent is extended or adjusted under 35 U.S.C. 154(b) by 385 days.

(21) Appl. No.: 12/381,317

(22) Filed: Mar. 9, 2009

(65) Prior Publication Data
US 2009/0234358 A1 Sep. 17, 2009

Related U.S. Application Data (63) Continuation of application No. PCT/EP2007/007848, filed on Sep. 8, 2007.

(30) Foreign Application Priority Data

Sep. 22, 2006 (DE) .......................... 10 2006 046 424

(51) Int. Cl.
*A61B 17/56* (2006.01)
(52) U.S. Cl. .............................. 606/71; 606/280; 606/70
(58) Field of Classification Search .......................... None
See application file for complete search history.

(56) References Cited

U.S. PATENT DOCUMENTS

| | | | |
|---|---|---|---|
| 3,693,616 A * | 9/1972 | Roaf et al. | 606/250 |
| 4,279,248 A * | 7/1981 | Gabbay | 606/71 |
| 4,670,938 A | 6/1987 | Fowlston | |
| 4,802,477 A | 2/1989 | Gabbay | |
| 5,549,620 A | 8/1996 | Bremer | |
| 5,620,452 A | 4/1997 | Yoon | |
| 5,722,976 A * | 3/1998 | Brown | 606/281 |
| 5,729,867 A | 3/1998 | Carmichael | |
| 5,800,436 A | 9/1998 | Lerch | |
| 5,928,231 A | 7/1999 | Klein et al. | |

(Continued)

FOREIGN PATENT DOCUMENTS

| | | |
|---|---|---|
| DE | 196 34 696 | 4/1998 |
| DE | 299 19 090 | 1/2000 |
| DE | 203 15 612 | 12/2003 |

(Continued)

OTHER PUBLICATIONS

*Patent Abstracts of Japan*, vol. 2003, No. 06, "Sacrum Fixing Device", Publication No. 2003038504, Publication Date Feb 12, 2003.

*Primary Examiner* — Thomas C. Barrett
*Assistant Examiner* — Melissa A Golob
(74) *Attorney, Agent, or Firm* — Lipsitz & McAllister, LLC (57) ABSTRACT

In a sternum closure device for fixing two sternum portions to be connected to one another, comprising an inner contact element for abutment on the inner surface of the sternum, at least one clamping element fixed to this contact element and projecting transversely from it and at least one outer contact element for abutment on the outer side of the sternum which can be clamped against the inner contact element by means of the clamping element guided through the intermediate space between the sternum portions, it is suggested in order to hinder the separation of the sternum as little as possible during any renewed operation that the inner contact element consist of two parts which are separate from one another and each of which is designed to abut on one of the two sternum portions and that connecting means be provided for the releasable connection of the two parts arranged next to one another.

38 Claims, 6 Drawing Sheets

U.S. PATENT DOCUMENTS

| | | | |
|---|---|---|---|
| 6,007,538 A * | 12/1999 | Levin | 606/71 |
| 6,022,351 A | 2/2000 | Bremer et al. | |
| 6,045,552 A | 4/2000 | Zucherman et al. | |
| 6,712,821 B2 | 3/2004 | Gabbay | |
| 7,361,178 B2 | 4/2008 | Hearn et al. | |
| 2005/0065521 A1 | 3/2005 | Steger et al. | |
| 2005/0234458 A1* | 10/2005 | Huebner | 606/69 |
| 2005/0278027 A1 | 12/2005 | Hyde, Jr. | |
| 2006/0122611 A1* | 6/2006 | Morales et al. | 606/72 |
| 2007/0038218 A1* | 2/2007 | Grevious | 606/71 |
| 2007/0250059 A1 | 10/2007 | Weisshaupt et al. | |

FOREIGN PATENT DOCUMENTS

| | | |
|---|---|---|
| DE | 103 26 690 | 1/2005 |
| DE | 10 2004 038 823 | 3/2006 |
| EP | 0 014 823 | 9/1980 |
| JP | 2003-220070 | 8/2003 |
| WO | 02/09602 | 2/2002 |
| WO | 2004/006783 | 1/2004 |
| WO | 2004/016205 | 2/2004 |
| WO | 2004/107998 | 12/2004 |
| WO | 2006/002744 | 1/2006 |

\* cited by examiner

STERNUM CLOSURE DEVICE

This application is a continuation of international application number PCT/EP2007/007848 filed on Sep. 8, 2007.

The present disclosure relates to the subject matter disclosed in international application number PCT/EP2007/007848 of Sep. 8, 2007 and German application number 10 2006 046 424.9 of Sep. 22, 2006, which are incorporated herein by reference in their entirety and for all purposes.

BACKGROUND OF THE INVENTION

The invention relates to a sternum closure device for fixing two sternum portions to be connected to one another, comprising an inner contact element for abutment on the inner surface of the sternum, at least one clamping element which is fixed to this contact element and projects transversely from it and at least one outer contact element for abutment on the outer side of the sternum which can be clamped against the inner contact element by means of the clamping element guided through the intermediate space between the sternum portions.

A sternum closure device of this type is described, for example, in DE 103 26 690 B4. It serves the purpose of fixing the two portions of the sternum, after they have been severed, in the position brought close to one another so that the two sternum portions can be connected to one another again osteally. Such a sternum closure device is of a very simple construction, is easy to apply and fixes the sternum portions securely and so the healing process is expedited.

In the case of a renewed operation, during which the sternum must again be severed along a line of separation, difficulties may, however, occur as a result of the known sternum closure devices since these can hinder any separation, for example, by sawing and are, themselves, difficult to remove since they can be surrounded by the new growth of bone material.

The object of the invention is to design a generic sternum closure device such that when the sternum is again severed the parts of the sternum closure device hinder the separation as little as possible.

SUMMARY OF THE INVENTION

This object is accomplished in accordance with the invention, in a sternum closure device of the type described at the outset, in that the inner contact element consists of two parts which are separate from one another and of which each is designed to abut on one of the two sternum portions and that connecting elements are provided for the releasable connection of the two parts arranged next to one another.

The outer contact elements can be removed relatively easily during any renewed operation; for this purpose it is sufficient to lift the clamping elements away. This is substantially more difficult in the case of the inner contact elements since these are not accessible. As a result of the construction of the inner contact elements from two parts which are separate from one another and of which each is associated with one sternum portion and as a result of the releasable connection of these two parts of the inner contact element, these two parts may be separated from one another after the connection is released and can, therefore, follow the separation of the sternum portions when these are spread apart. As a result, the inner contact elements do not hinder this spreading apart of the two sternum portions.

When abutting on the inner surface of the sternum portions, each part of the inner contact element can have fixing projections which penetrate the sternum portions and so the two parts of the inner contact element can be secured on the sternum portions before they are clamped against one another by a clamping device following an operation.

It is favorable when the parts of the inner contact element have an essentially flat contact surface for abutment on the inner surface of the sternum portions.

The clamping elements can, in particular, be of a pin-shaped design.

In a first, preferred embodiment, it is provided for clamping elements to be arranged on each of the two parts of the inner contact element and for the outer contact elements to each be connected to clamping elements of both parts of the inner contact element so that the two parts of the inner contact element are held together by the outer contact element, located next to one another.

The outer contact elements therefore form a bridge between the two parts of the inwardly located contact element; this bridge is connected to the two parts of the inner contact element by the clamping elements and so the two sternum portions are fixed in the position clamped together, on the one hand, by this connection and, on the other hand, by the outer contact element.

During a renewed operation, the outer contact elements can be removed and the two parts of the inner contact element are then no longer connected to one another; the sternum portions can be spread apart quite easily after they have been severed with a bone saw.

It may be provided for the clamping elements to be connected to the parts of the inner contact element in an area of these parts which projects in the direction towards the respectively other part and for these projecting areas of the parts of the inner contact element to be offset relative to one another in longitudinal direction of the intermediate space between the sternum portions. In this way, it is possible for the clamping elements to be arranged more or less in a linear manner along the intermediate space between the two sternum portions, wherein the respectively projecting areas of the two parts of the inner contact element which bear the clamping elements bridge this intermediate space alternatingly.

The projecting areas may, for example, be of a triangular design and be connected to the clamping element in the area of the tip of the triangle.

It is particularly advantageous when a plurality of clamping elements are arranged on each of the two parts of the inner contact element so as to follow one another in longitudinal direction of the intermediate space between the sternum portions. The parts of the inner contact element can extend over the entire height of the sternum and then bear a greater number of consecutive connecting elements, for example, four or five connecting elements.

In this respect, it is favorable when a plurality of outer contact elements are provided, each of which is connected to a clamping element of both the one and the other parts of the inner contact element. Whereas the inner contact element then extends over a greater length of the intermediate space between the sternum portions, this is not the case for the outer contact elements; each of them merely connects a clamping element of both the one part and the other part of the inner contact element.

In a further, preferred embodiment, it is provided for the two parts of the inner contact element to have areas abutting areally on one another and for the connecting elements to releasably connect the two parts to one another in these areas. As a result, great stability of the inner contact element is obtained and after release of the connecting elements both parts of the inner contact element can easily be separated from one another, following the spreading movement of the sternum portions.

The two parts can, for example, be screwed to one another by threaded screws.

It is particularly advantageous when the threaded screws are formed by the clamping elements. During any renewed operation, the clamping elements can be screwed out of the inner contact element once the outer contact elements have been removed and, as a result, release the connection between the two parts of the inner contact element.

It is favorable when the two parts of the inner contact element have prong-like projections on the sides facing the respectively other part and when these prong-like projections are offset relative to one another in longitudinal direction of the intermediate space between the sternum portions and engage in one another in such a manner that the prong-like projections of the one part engage under the respectively other part. As a result, great stability of the inner contact element is obtained when the two parts are clamped against one another by the connecting elements.

In another embodiment, it may be provided for one of the two parts of the inner contact element to have, on its side facing the other part, prong-like projections which dip into recesses in the other part and engage under the other part.

The inner contact element is preferably connected to two clamping elements which are offset in longitudinal direction of the intermediate space between the sternum portions. This results in a positioning aid during insertion of the inner contact elements and in the case of embodiments, in which the clamping elements releasably connect the two parts of the inner contact element to one another, it is ensured that the two parts of the inner contact element are connected to one another so as to be non-rotatable.

It may be provided for the contact elements to be coated with a material which prevents the bonding to bone material, for example, with polytetrafluoroethylene. As a result, it is easier to detach the contact elements from the surrounding bone material if a renewed separation of the sternum is necessary.

The following description of preferred embodiments of the invention serves to explain the invention in greater detail in conjunction with the drawings.

DETAILED DESCRIPTION OF THE INVENTION

Figure 1:
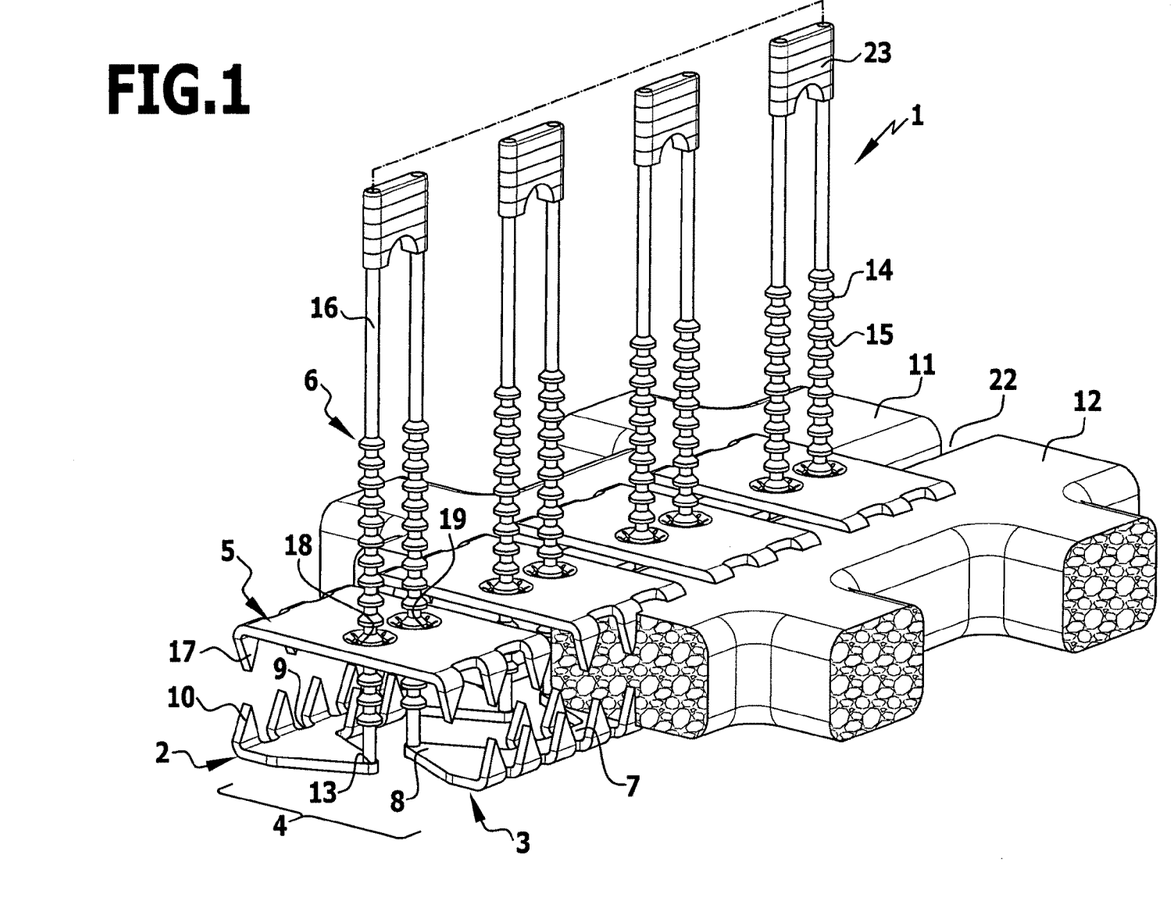
FIG. 1: shows a perspective view of a first preferred embodiment of a sternum closure device with an inner contact element, which consists of two separate parts, in the applied position prior to the shortening of the pin-shaped clamping elements.
Figure 2:
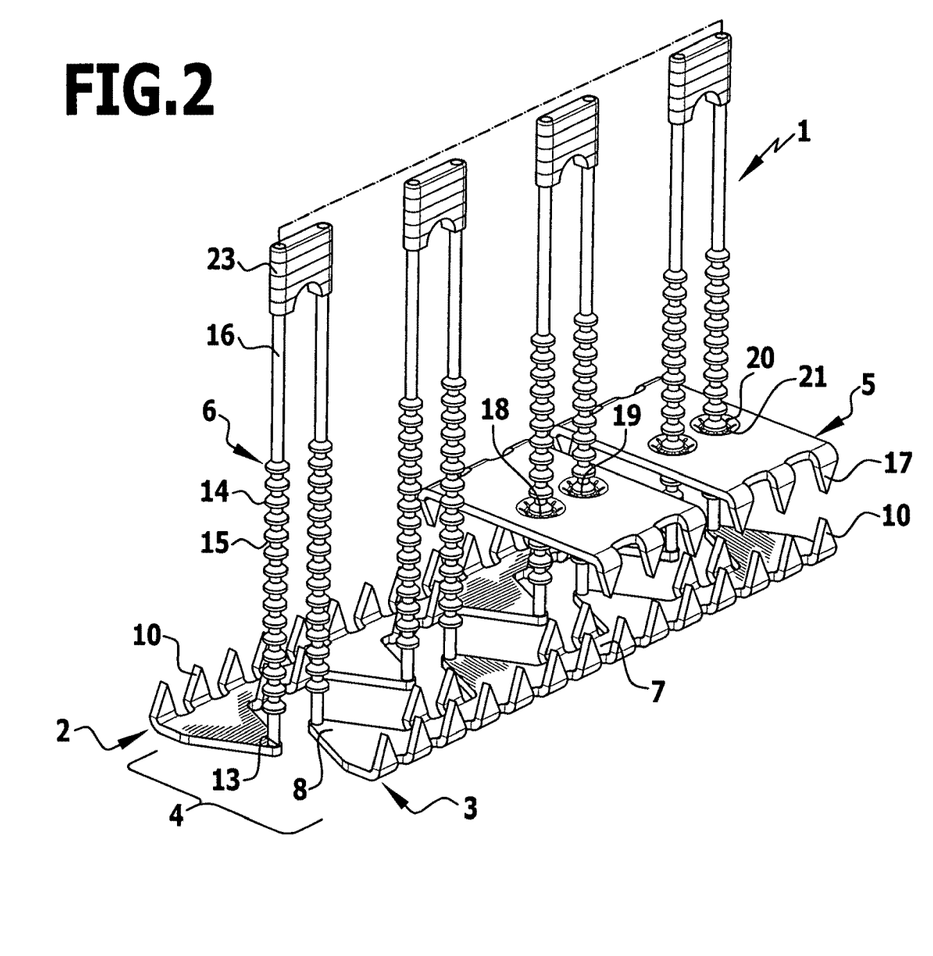
FIG. 2: shows a view similar to FIG. 1, wherein two outer contact elements and the bone material are omitted to increase clarity.
Figure 3:
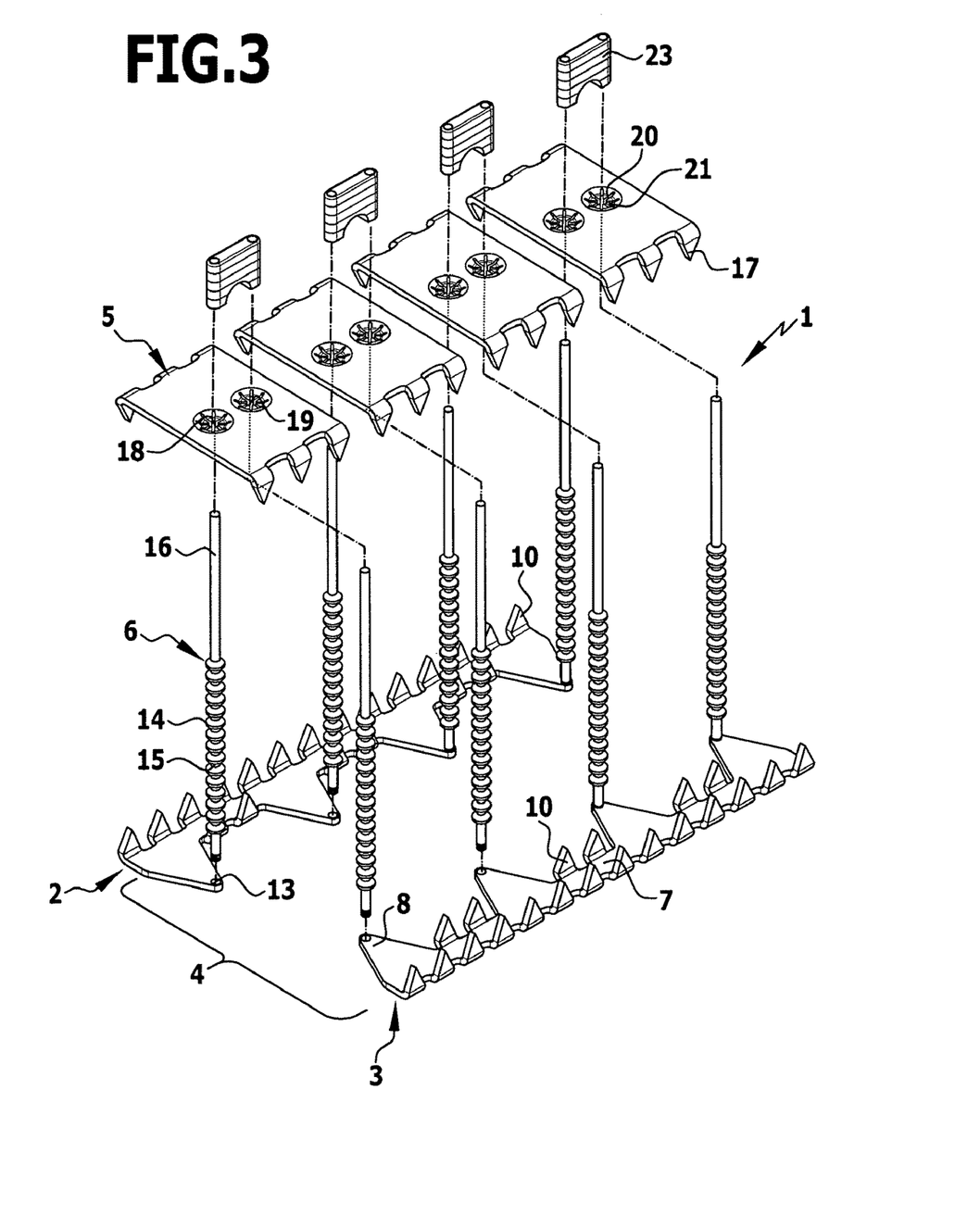
FIG. 3: shows a perspective view of the sternum closure device of FIG. 1 prior to assembly of the individual parts.

The sternum closure device 1 illustrated in FIGS. 1 to 3 comprises an inner contact element 4 consisting of two parts 2, 3, a number of outer contact elements 5 as well as snap-in pins 6 secured to the parts 2, 3 of the inner contact element 4. The two parts 2, 3 of the inner contact element 4 are of the same construction; for this reason, only one of the two will be described in detail in the following. The part 2 has an elongated, plate-like and flat web 7, from which triangular connecting areas 8 project to one side and are arranged at a distance to one another in longitudinal direction of the web 7. Pointed projections 10, which are bent upwards and serve to fix the parts 2, 3 on the inner surface of a sternum portion 11 and 12, respectively, project at right angles to the surface of the web 7 between the connecting areas 8, on the one hand, and on the oppositely located longitudinal side 9 of the web 7, on the other hand, which faces away from the connecting areas 8.

In the area of the tips of the triangular connecting areas 8, these are connected to the snap-in pins 6; the snap-in pins 6 project upwards at right angles from the surface of the webs 7 and can be screwed, for example, into threaded bores 13 of the connecting areas 8 or riveted to them or connected in a different way. The snap-in pins 6 have, in their lower part, a snap-in section 15 which is provided with circumferential ribs 14 and a smooth extension section 16 adjoining thereto.

The outer contact elements 5 are of a rectangular and plate-like design; at two oppositely located edges they have pointed projections 17 which are bent down at right angles and likewise provided for engagement in the sternum portions 11, 12. Two openings 18, 19 of the same design are arranged in the flat part of the outer contact elements 5 and their edges have notches 20 which extend radially outwards so that the edge areas are subdivided into tongues 21 which can be bent separately from one another.

The contact elements and the snap-in pins are produced from metal; in this respect, biocompatible metals are used, for example, titanium or titanium alloys.

In addition, the contact elements can be coated, in particular, with a coating which prevents the adhesion of bone material to a great extent; for example, this coating can consist of polytetrafluoroethylene.

When the sternum closure device of FIGS. 1 to 3 is applied, the two parts 2, 3 of the inner contact element 4 are, first of all, with sternum portions 11, 12 spread apart from one another, positioned with the snap-in pins 6 inserted into them on the inner surface of the two sternum portions 11, 12 such that the snap-in pins 6 are arranged along the edge of the sternum portions 11, 12 and as a result of the parts 2, 3 being pressed onto the inner surface of the sternum portions 11, 12 the projections 10 of the parts 2, 3 bite into the bone material. As a result, the parts 2, 3 are held in abutment on the inner surface of the sternum portions 11, 12.

The two parts 2, 3 are positioned on the sternum portions 11, 12 such that the connecting areas 8 of the two parts 2, 3 are offset relative to one another in longitudinal direction of the intermediate space 22 between the two sternum portions 11, 12, i.e., the connecting areas 8 of the one part 2 engage between the connecting areas 8 of the other part 3. This positioning can be achieved, for example, with the aid of a template not illustrated in the drawings.

In a next step, the two sternum portions 11, 12 are clamped against one another with the aid of a clamping device not illustrated in the drawings, for example, with the aid of clamping forceps such that the width of the intermediate space 2 is reduced. The two parts 2, 3 are, as a result, likewise brought closer to one another until the snap-in pins 6 of the two parts 2, 3 are approximately located on one line, i.e., until the width of the intermediate space 22 is reduced to such an extent that it corresponds approximately to the diameter of the snap-in pins 6. In this position, an outer contact element 5 is pushed each time onto two respective snap-in pins 6 located next to one another in longitudinal direction of the intermediate space 22 so that the extension sections 16 enter the openings 18, 19. In this respect, each outer contact element 5 is penetrated by a snap-in pin 6 which is held on one part 2 of the inner contact element 4 and by a second snap-in pin 6 which is held on the other part 3 of the inner contact element 4.

The outer contact element 5 is then moved in the direction towards the inner contact element 4 by means of a suitable tool which is likewise not illustrated in the drawings, wherein the tongues 21 of the opening 18 slide past the circumferential ribs 14 of the snap-in section 15 of the snap-in pins 6. This movement continues until the projections 17 of the outer contact element 5 penetrate the bone material of the two sternum portions 11, 12 and until the outer contact element 5 abuts areally on the outer side of the two sternum portions 11, 12. In this position, inner contact element and the outer contact elements 5 are clamped against one another.

This clamping procedure can be assisted by the fact that bridge-like stops 23 are placed on the extension sections 16 and the instrument which moves the outer contact element 5 in the direction towards the inner contact element 4 is applied to these stops.

As soon as the outer contact elements 5 are clamped against the inner contact element 4, the snap-in pins 6 are removed directly above the outer contact elements 5, for example, with the aid of cutting forceps. The outer contact elements 5 are secured in the position once reached by the engagement of the tongues 21 in the circumferential ribs 14 and so, as a result, the two sternum portions 11, 12 are also clamped permanently against one another.

During any renewed operation, the outer contact elements 5 are removed, first of all, from the outer side of the sternum. As a result, the parts 2, 3 of the inner contact element 4, which were connected to one another via the snap-in pins 6 via the outer contact elements 5 acting as a bridge, are also separated from one another.

Once the sternum has been severed with the aid of a bone saw, the portions 11, 12 of the sternum can, therefore, be spread apart easily; this movement is not hindered in any way by the inner contact element 4 since the two parts of the inner contact element 4 are no longer connected to one another.

Once the portions of the sternum have been spread apart, the inner contact elements 4 will be released from the inner surface of the sternum portions 11, 12 and removed completely so that access to the interior of the body is available through the intermediate space 22 without any hindrance by parts of the sternum closure device.

In the embodiment of FIGS. 1 to 3, the parts 2, 3 of the inner contact element 4 are connected to one another only via the snap-in pins 6 and the outer contact elements 5 placed thereon.

Figure 4:
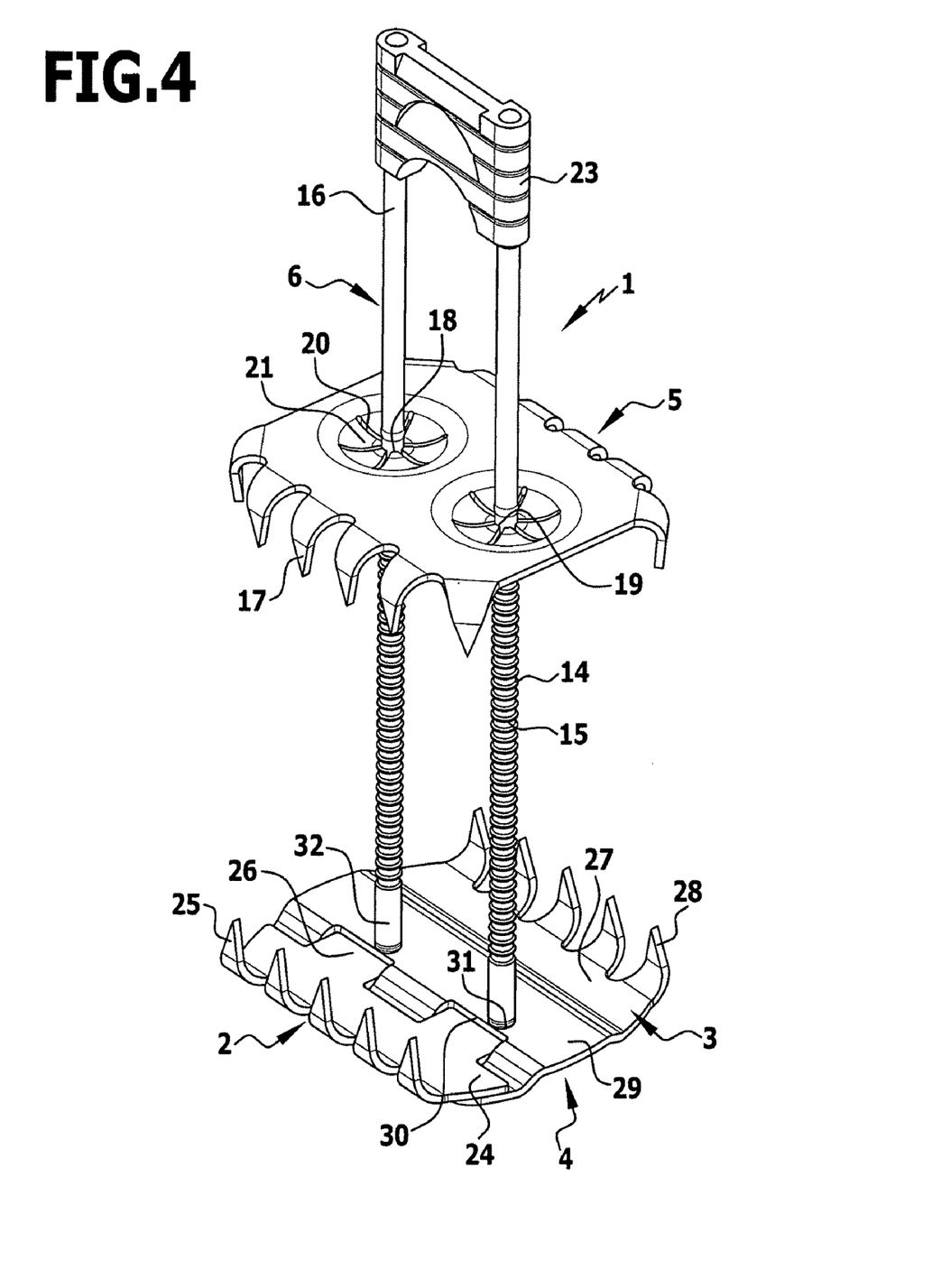
FIG. 4: shows a further preferred embodiment of a sternum closure device with a divisible inner contact element.
Figure 5:
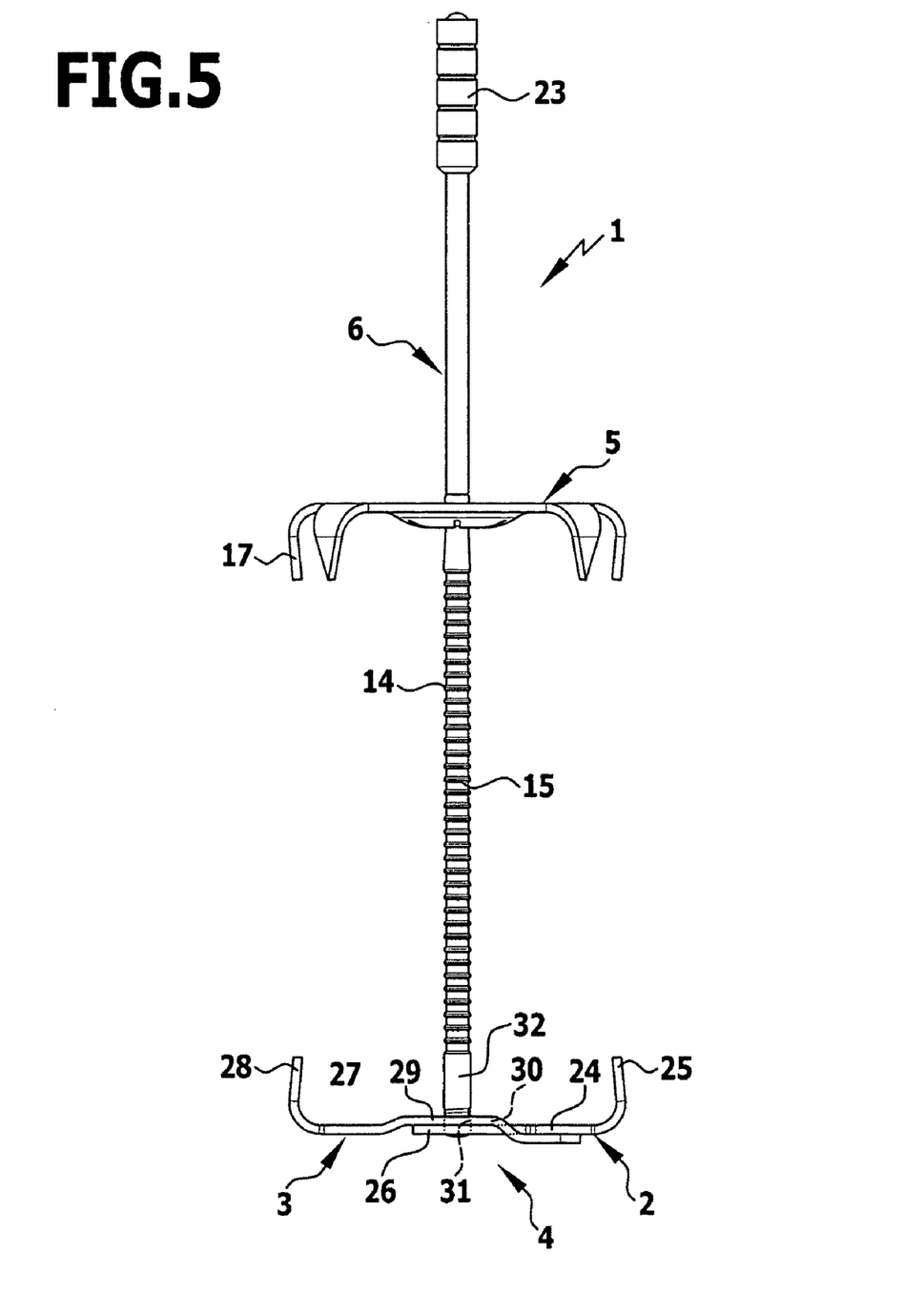
FIG. 5: shows a side view of the sternum closure device of FIG. 4.
Figure 6:
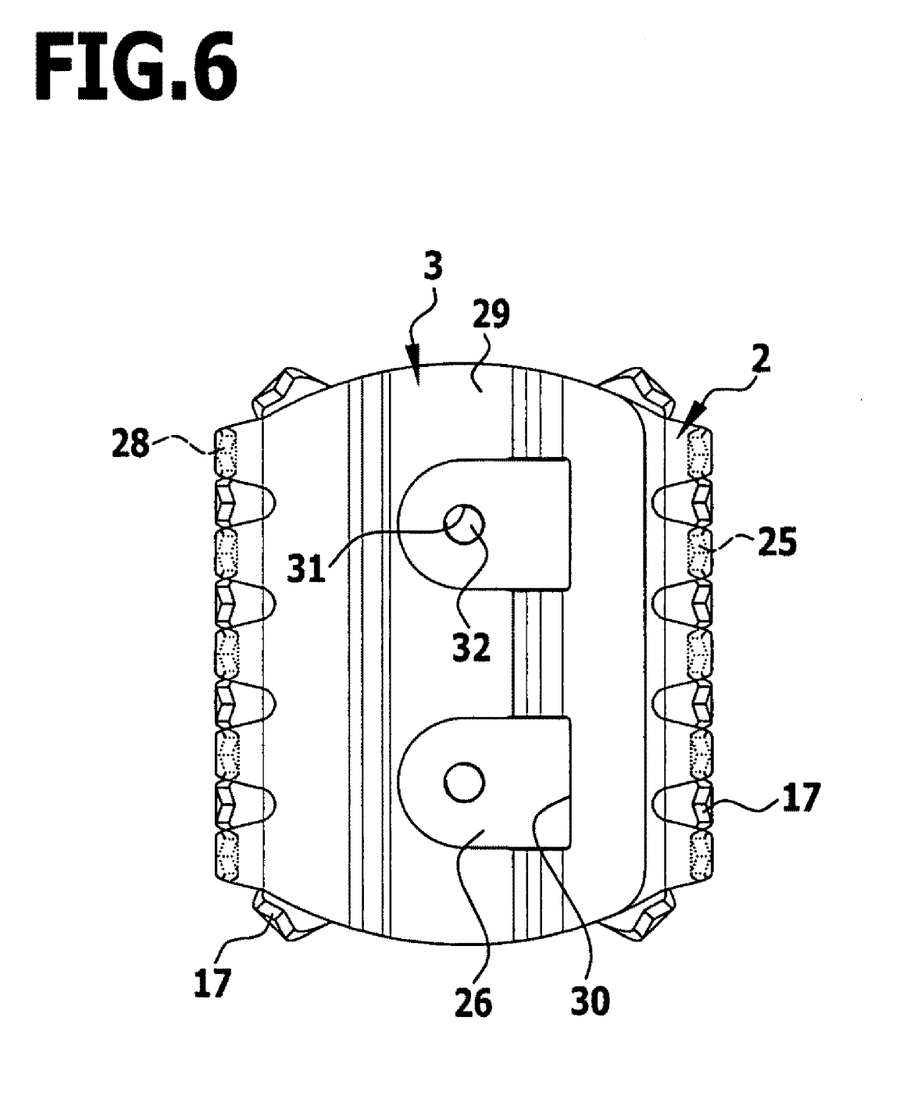
FIG. 6: shows a view of the sternum closure device of FIG. 4 from below.

In contrast thereto, the sternum closure device of FIGS. 4 to 6, in which corresponding parts have the same reference numerals, has an inner contact element 4 with two parts 2, 3 which abut directly on one another and are releasably connected to one another.

One part 2 of the inner contact element 4 forms a flat, essentially rectangular contact surface 24 which, at the outer edge, has pointed projections 25 which project upwards and, on the oppositely located side, prong-like tongues 26 which are located in the plane of the contact surface 24 and are arranged at a distance from one another.

The other part 3 likewise has a largely flat contact surface 27 and, at the externally located longitudinal edge, pointed projections 28 which project upwards; the contact surface 26 is, in this respect, twice bent at an angle so that a slightly raised central area 29 results (FIG. 5). Through openings 30 for the tongues 26 of the part 2 are arranged in the area of transition between this central area 29, on the one hand, and the projections 27, on the other hand. The tongues 26 can be pushed through these openings 30 and then abut areally on the underside of the raised central area 29 while the part of the contact surface 27 which is located opposite the projections 28 comes to rest areally on the underside of the part 2.

Threaded bores 31 are arranged in the central area 29 and in the tongues 26 and the lower end 32 of a snap-in pin 6 which has a corresponding external thread is screwed into these bores so that, as a result, the two parts 2, 3 are securely connected to one another.

In the embodiment illustrated, the part 2 has two tongues 26 located next to one another and the part 3 has two corresponding through openings 30 so that two snap-in pins 6 are screwed into the inner contact element 4 and, as a result, the two parts 2, 3 are securely connected to one another.

The sternum closure device of FIGS. 4 to 6 can be preassembled in this way; in this respect, the outer contact element 5 is pushed onto the extension sections 16 and the extension sections 16 are connected to one another at their free ends via a bridge-like stop 23. In this configuration, the preassembled sternum closure device 1 can be inserted once the sternum portions 11, 12 have been spread apart and then be fixed to them in the conventional manner once the sternum portions 11, 12 have been clamped together in that the inner contact element 4 is pressed against the inner surface. The outer contact element 5 is then clamped against the inner contact element 4 in the manner described by means of a clamping instrument engaging on the stop 23 and the protruding snap-in pins 6 removed.

In the case of any renewed operation, the outer contact elements 5 are removed first of all in the same way as in the embodiment of FIGS. 1 to 3 and, subsequently, the snap-in pins 6 are screwed out of the threaded bores 31 by means of a suitable instrument. As a result, the two parts 2, 3 of the inner contact element 4 are separated from one another so that they can be drawn apart transversely to the longitudinal direction of the intermediate space, i.e., in spreading direction of the sternum portions 11, 12. This spreading takes place after the sternum has been severed with a bone saw, wherein this procedure is not hindered in any way by the remaining inner contact elements 4 once the outer contact elements 5 and the snap-in pins 6 have been removed.

Once the sternum portions 11, 12 have been spread apart the parts 2, 3 can be released from the inner surface of the sternum and removed.

The invention claimed is:

1. Sternum closure device for fixing two sternum portions to be joined to one another, comprising:
an inner contact element for abutment on an inner surface of a sternum,
at least one clamping element being fixed to said inner contact element and projecting transversely from said inner contact element, and
at least one outer contact element for abutment on an outer side of the sternum, said at least one outer contact element being clampable against the inner contact element by means of the clamping element guided through an intermediate space between the two sternum portions, wherein:
the inner contact element consists of two parts separate from one another, each of the two parts being designed to abut on one of the two sternum portions, and
connecting elements are provided for the releasable connection of the two parts arranged next to one another,
the two parts of the inner contact element have areas abutting areally on one another,
the connecting elements releasably connect the two parts to one another in the abutting areas,
the two parts are screwed to one another by threaded screws, and
the threaded screws are formed by the clamping elements.

2. Sternum closure device as defined in claim 1, wherein during abutment on the inner surface of the two sternum portions, each of the two parts has fixing projections penetrating said portions.

3. Sternum closure device as defined in claim 1, wherein the two parts have an essentially flat contact surface for abutment on the inner surface of the two sternum portions.

4. Sternum closure device as defined in claim 1, wherein the at least one clamping element is of a pin-shaped design.

5. Sternum closure device as defined in claim 1, wherein:
the connecting elements comprise prong-like projections on sides of each of the two parts facing the respective other part, and
the prong-like projections are offset relative to one another in a longitudinal direction of the intermediate space between the two sternum portions and engage in one another in such a manner that the prong-like projections of the one part engage under the respectively other part.

6. Sternum closure device as defined in claim 1, wherein the connecting elements comprise prong-like projections on a side of one of the two parts of the inner contact element facing the other part and corresponding recesses in a side of the other of the two parts, said projections of the one part dipping into said recesses and engaging beneath the other part.

7. Sternum closure device as defined in claim 1, wherein the inner contact element is connected to two clamping elements offset in a longitudinal direction of the intermediate space between the two sternum portions.

8. Sternum closure device as defined in claim 1, wherein the contact elements are coated with a material which prevents bonding to bone material.

9. Sternum closure device as defined in claim 8, wherein the contact elements are coated with polytetrafluoroethylene.

10. Sternum closure device for fixing two sternum portions to be joined to one another, comprising:
an inner contact element for abutment on an inner surface of a sternum,
at least one clamping element being fixed to said inner contact element and projecting transversely from said inner contact element, and
at least one outer contact element for abutment on an outer side of the sternum, said at least one outer contact element being clampable against the inner contact element by means of the at least one clamping element guided through an intermediate space between the two sternum portions,
wherein:
the inner contact element consists of two parts separate from one another, each of the two parts being designed to abut on one of the two sternum portions,
connecting elements are provided for the releasable connection of the two parts arranged next to one another, clamping elements are arranged on each of the two parts of the inner contact element,
each of the at least one outer contact elements are connected to the respective clamping elements of both parts of the inner contact element such that the two parts of the inner contact element are held together by the at least one outer contact element such that the two parts are located next to one another,
the respective clamping elements are connected to the two parts of the inner contact element in an area of the two parts projecting in the direction towards the respectively other part, and
the projecting areas of the two parts of the inner contact element are offset relative to one another in a longitudinal direction of the intermediate space between the two sternum portions.

11. Sternum closure device as defined in claim 10, wherein a plurality of clamping elements are arranged on each of the two parts of the inner contact element so as to follow one another in a longitudinal direction of the intermediate space between the sternum portions.

12. Sternum closure device as defined in claim 11, wherein a plurality of outer contact elements are provided, each of said contact elements being connected to the respective clamping element of both the one and the other parts of the inner contact element.

13. Sternum closure device as defined in claim 10, wherein the projecting areas are of a triangular design and are connected to the clamping elements in an area of a tip of a triangle of the triangular design.

14. Sternum closure device as defined in claim 10, wherein during abutment on the inner surface of the two sternum portions, each of the two parts has fixing projections penetrating said portions.

15. Sternum closure device as defined in claim 14, wherein the two parts are screwed to one another by threaded screws.

16. Sternum closure device as defined in claim 15, wherein the threaded screws are formed by the at least one clamping element.

17. Sternum closure device as defined in claim 10, wherein the two parts have an essentially flat contact surface for abutment on the inner surface of the two sternum portions.

18. Sternum closure device as defined in claim 10, wherein the at least one clamping element is of a pin-shaped design.

19. Sternum closure device as defined in claim 10, wherein the contact elements are coated with a material which prevents bonding to bone material.

20. Sternum closure device as defined in claim 19, wherein the contact elements are coated with polytetrafluoroethylene.

21. Sternum closure device for fixing two sternum portions to be joined to one another, comprising:
an inner contact element for abutment on an inner surface of a sternum,
at least one clamping element being fixed to said inner contact element and projecting transversely from said inner contact element, and
at least one outer contact element for abutment on an outer side of the sternum, said at least one outer contact element being clampable against the inner contact element by means of the at least one clamping element guided through an intermediate space between the two sternum portions,
wherein:
the inner contact element consists of two parts separate from one another, each of the two parts being designed to abut on one of the two sternum portions, connecting elements are provided for the releasable connection of the two parts arranged next to one another, the two parts of the inner contact element have areas abutting areally on one another, the connecting elements releasably connect the two parts to one another in the abutting areas, the connecting elements comprise prong-like projections on sides of each of the two parts facing the respective other part, and the prong-like projections are offset relative to one another in a longitudinal direction of the intermediate space between the two sternum portions and engage in one another in such a manner that the prong-like projections of the one part engage under the respectively other part.

22. Sternum closure device as defined in claim 21, wherein during abutment on the inner surface of the two sternum portions, each of the two parts has fixing projections penetrating said portions.

23. Sternum closure device as defined in claim 21, wherein the two parts have an essentially flat contact surface for abutment on the inner surface of the two sternum portions.

24. Sternum closure device as defined in claim 21, wherein the at least one clamping element is of a pin-shaped design.

25. Sternum closure device as defined in claim 21, wherein the prong-like projections on each of the respective sides of the two parts of the inner contact element dip into corresponding recesses on each of the other respective sides of the two parts, such that the prong like projections of each part engage beneath the other part.

26. Sternum closure device as defined in claim 21, wherein the inner contact element is connected to two clamping elements offset in a longitudinal direction of the intermediate space between the two sternum portions.

27. Sternum closure device as defined in claim 21, wherein the contact elements are coated with a material which prevents bonding to bone material.

28. Sternum closure device as defined in claim 27, wherein the contact elements are coated with polytetrafluoroethylene.

29. Sternum closure device for fixing two sternum portions to be joined to one another, comprising:

an inner contact element for abutment on an inner surface of a sternum, at least one clamping element being fixed to said inner contact element and projecting transversely from said inner contact element, and at least one outer contact element for abutment on an outer side of the sternum, said at least one outer contact element being clampable against the inner contact element by means of the at least one clamping element guided through an intermediate space between the two sternum portions, wherein:

the inner contact element consists of two parts separate from one another, each of the two parts being designed to abut on one of the two sternum portions, connecting elements are provided for the releasable connection of the two parts arranged next to one another, the two parts of the inner contact element have areas abutting areally on one another, the connecting elements releasably connect the two parts to one another in the abutting areas, and the connecting elements comprise prong-like projections on a side of one of the two parts of the inner contact element facing the other part and corresponding recesses in a side of the other of the two parts, said projections of the one part dipping into said recesses and engaging beneath the other part.

30. Sternum closure device as defined in claim 29, wherein during abutment on the inner surface of the two sternum portions, each of the two parts has fixing projections penetrating said portions.

31. Sternum closure device as defined in claim 29, wherein the two parts have an essentially flat contact surface for abutment on the inner surface of the two sternum portions.

32. Sternum closure device as defined in claim 29, wherein the at least one clamping element is of a pin-shaped design.

33. Sternum closure device as defined in claim 29, wherein the two parts are screwed to one another by threaded screws.

34. Sternum closure device as defined in claim 33, wherein the threaded screws are formed by the at least one clamping element.

35. Sternum closure device as defined in claim 29, wherein:

the prong-like projections are disposed on sides of each of the two parts facing the respective other part, and the prong-like projections are offset relative to one another in a longitudinal direction of the intermediate space between the two sternum portions and engage in one another in such a manner that the prong-like projections of the one part engage under the respectively other part.

36. Sternum closure device as defined in claim 29, wherein the inner contact element is connected to two clamping elements offset in a longitudinal direction of the intermediate space between the two sternum portions.

37. Sternum closure device as defined in claim 29, wherein the contact elements are coated with a material which prevents bonding to bone material.

38. Sternum closure device as defined in claim 37, wherein the contact elements are coated with polytetrafluoroethylene.

* * * * *